(12) United States Patent
Wallace et al.

(10) Patent No.: US 6,860,893 B2
(45) Date of Patent: Mar. 1, 2005

(54) STABLE COIL DESIGNS

(75) Inventors: Michael P. Wallace, Pleasanton, CA (US); Marc-Alan Levine, San Francisco, CA (US); Delilah Yin Hui, Union City, CA (US); Mary M. Chen, San Leandro, CA (US); Liem Ho, Mountain View, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 219 days.

(21) Appl. No.: 09/974,068

(22) Filed: Oct. 9, 2001

(65) Prior Publication Data

US 2002/0019647 A1 Feb. 14, 2002

Related U.S. Application Data

(63) Continuation of application No. 09/018,278, filed on Feb. 4, 1998, now Pat. No. 6,322,576, which is a continuation-in-part of application No. 08/924,010, filed on Aug. 29, 1997, now abandoned.

(51) Int. Cl.$^7$ .............................................. A61M 29/00
(52) U.S. Cl. ...................................................... 606/200
(58) Field of Search ................................ 606/151, 157, 606/158, 191, 195, 198, 200, 194; 623/1.1, 1.15, 1.18, 1.2, 1.21, 1.22

(56) References Cited

U.S. PATENT DOCUMENTS

| | | |
|---|---|---|
| 3,174,851 A | 3/1965 | Buehler et al. |
| 3,351,463 A | 11/1967 | Rozner et al. |
| 3,753,700 A | 8/1973 | Harrison et al. |
| 4,994,069 A | 2/1991 | Ritchart et al. |
| 5,122,136 A | 6/1992 | Guglielmi et al. |
| 5,226,911 A | 7/1993 | Chee et al. |
| 5,234,437 A | 8/1993 | Sepetka |
| 5,250,071 A | 10/1993 | Palermo |
| 5,261,916 A | 11/1993 | Engelson |
| 5,304,194 A | 4/1994 | Chee et al. |
| 5,304,195 A | 4/1994 | Twyford, Jr. et al. |
| 5,312,415 A | 5/1994 | Palermo |
| 5,334,210 A | 8/1994 | Gianturco |
| 5,350,397 A | 9/1994 | Palermo et al. |
| 5,354,295 A | 10/1994 | Guglielmi et al. |
| 5,382,259 A | 1/1995 | Phelps et al. |
| 5,522,836 A | 6/1996 | Palermo |
| 5,527,338 A | 6/1996 | Purdy |
| 5,536,274 A | 7/1996 | Neuss |
| 5,624,461 A * | 4/1997 | Mariant ...................... 606/191 |
| 5,639,277 A | 6/1997 | Mariant et al. |
| 5,645,082 A | 7/1997 | Sung et al. |
| 5,645,558 A | 7/1997 | Horton |
| 5,649,949 A | 7/1997 | Wallace et al. |
| 5,749,891 A * | 5/1998 | Ken et al. ..................... 606/200 |

FOREIGN PATENT DOCUMENTS

| | | |
|---|---|---|
| DE | 32 03 410 A1 | 11/1982 |
| EP | 0 747 014 A1 | 12/1996 |
| EP | 0 765 636 A2 | 4/1997 |

* cited by examiner

*Primary Examiner*—David O. Reip
(74) *Attorney, Agent, or Firm*—Bingham McCuthchen LLP

(57) ABSTRACT

This is an implantable vaso-occlusive device. The device has a complex, three-dimensional structure in a relaxed configuration that may be used in the approximate shape of an anatomical cavity. It may be deployed in the approximate shape of a sphere, an ovoid, a clover, a box-like structure or other distorted spherical shape. The loops forming the relaxed configuration may pass through the interior of the structure. The device is a self-forming shape made from a pre-formed linear vaso-occlusion member. Fibers may be introduced onto the device and affixed to the pre-formed linear member. The constituent member may be also be covered with a fibrous braid. The device is typically introduced through a catheter. The device is passed axially through the catheter sheath and assumes its form upon exiting the catheter without further action. The invention also includes methods of winding the anatomically shaped vaso-occlusive device into appropriately shaped forms and annealing them to form various devices.

33 Claims, 14 Drawing Sheets

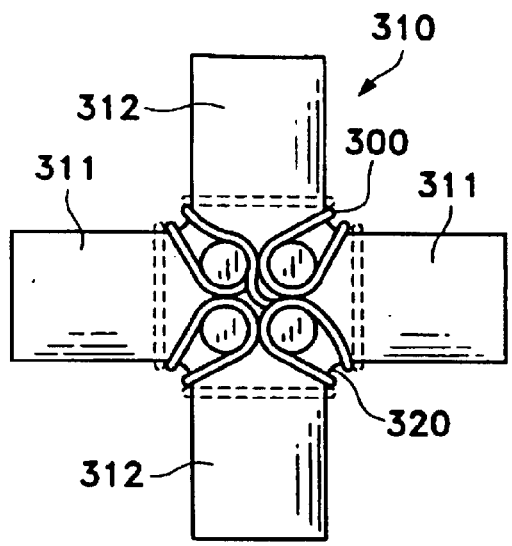
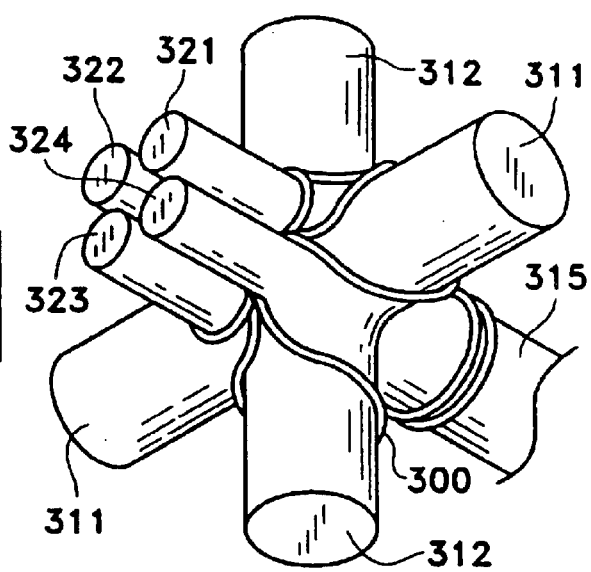
Fig. 3A
Fig. 3B
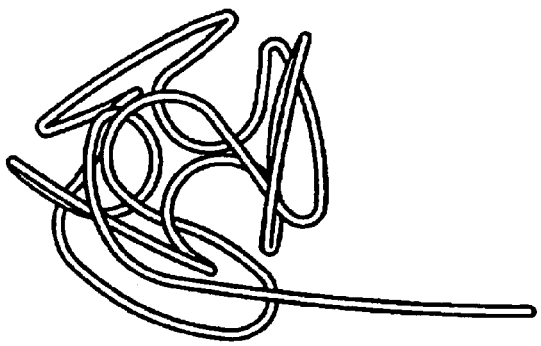
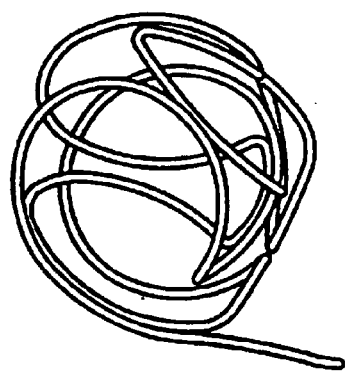
Fig. 4A
Fig. 4B
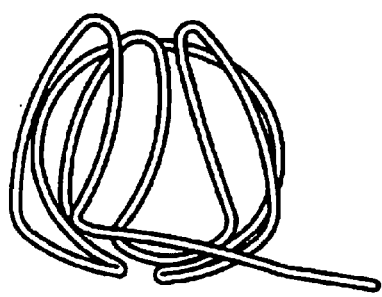
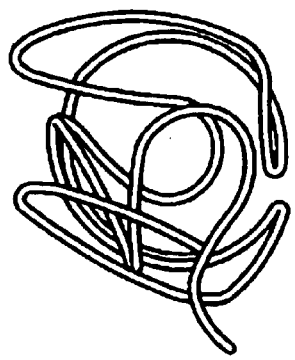
Fig. 4C
Fig. 4D

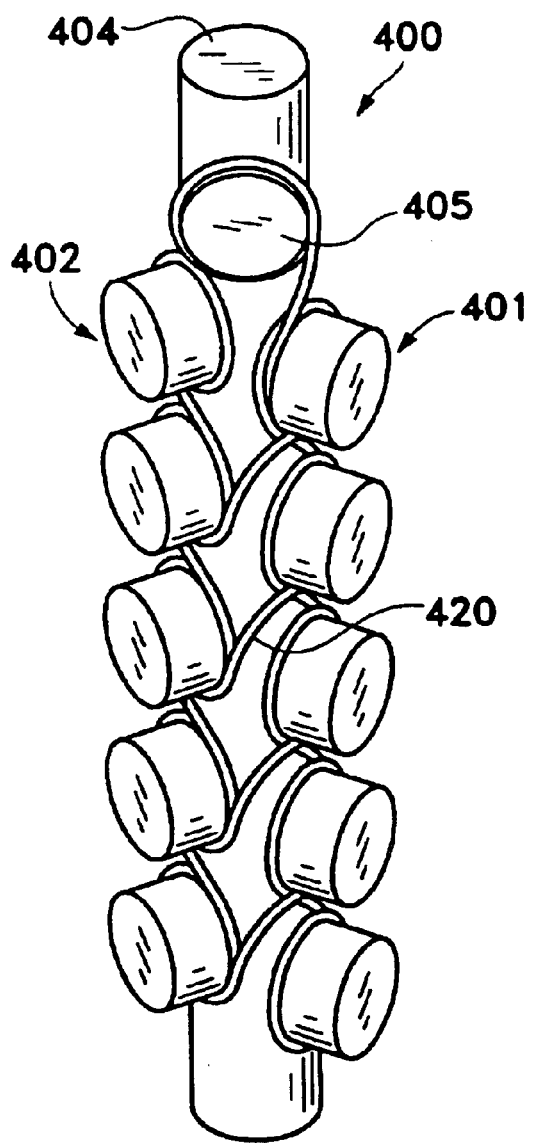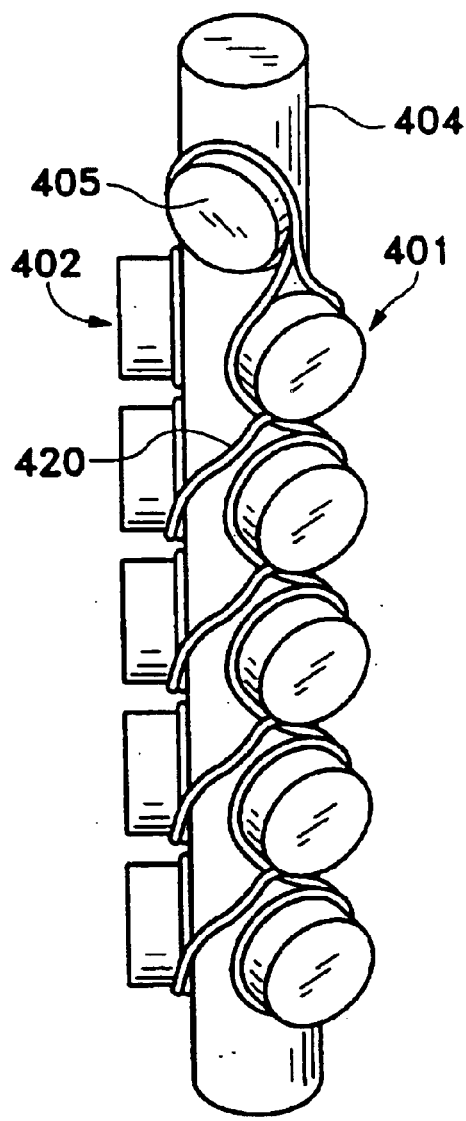
Fig. 7A            Fig. 7B
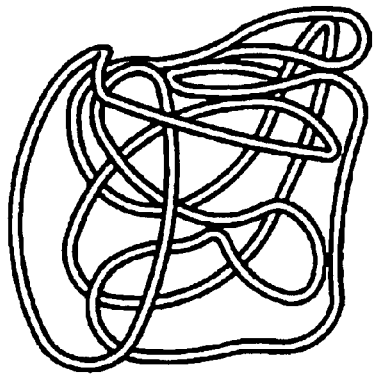
Fig. 7C

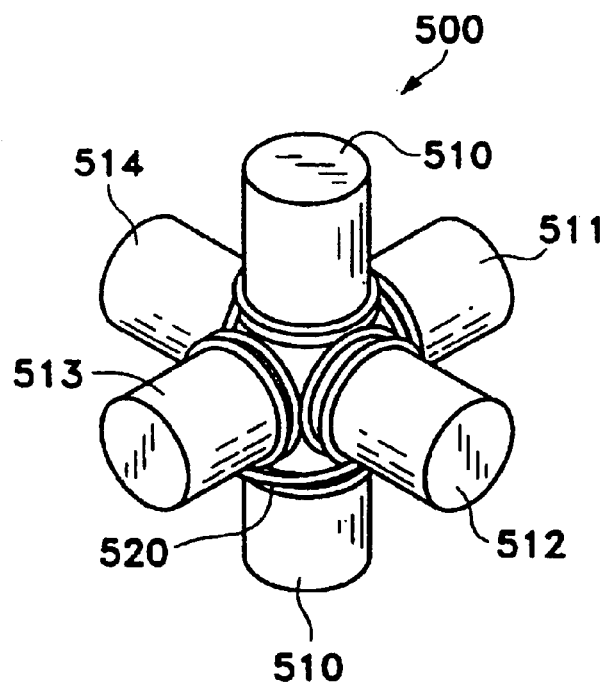
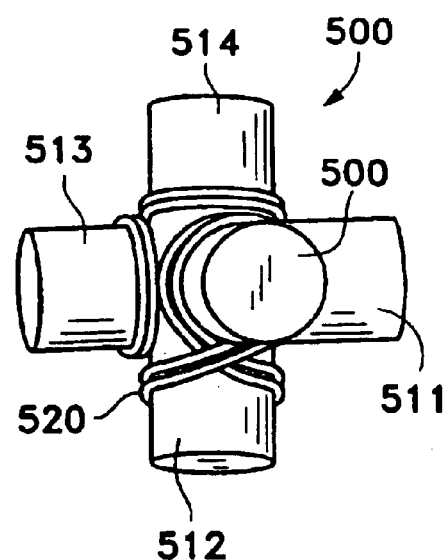
Fig. 9A         Fig. 9B
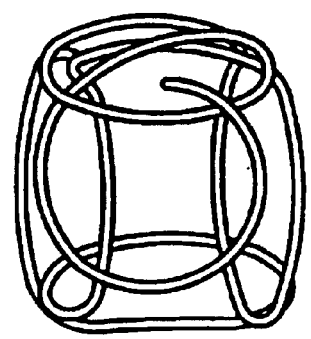
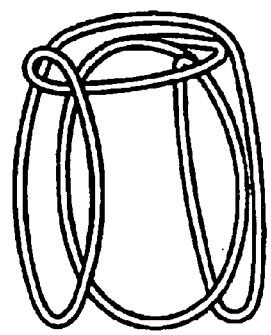
Fig. 10A        Fig. 10B

STABLE COIL DESIGNS

RELATED APPLICATIONS

This application is a continuation of U.S. patent application Ser. No. 09/018,278 filed Feb. 4, 1998, now U.S. Pat. No. 6,322,576 which is a continuation-in-part of U.S. patent application Ser. No. 08/924,010, filed Aug. 29, 1997 now abandoned.

FIELD OF THE INVENTION

This invention is an implantable vaso-occlusive device. More particularly, it is a vaso-occlusive device which, in a relaxed configuration, has a stable three-dimensional structure which may be used to fill an anatomical cavity. The vaso-occlusion member may be one or more strands of a helical coil or braid variously comprising a suitable metal, or, in the case of a braid, such metal may be co-woven with various polymeric or natural fibers. The relaxed configurations are comprises of a series of overall shapes including spherical, elliptical, oval, clover or box-like. The relaxed configurations may be substantially hollow or may have one or more strands or loops of the coil passing though the interior of the structure. The device is a self-forming shape made from a pre-formed vaso-occlusion member.

BACKGROUND OF THE INVENTION

Vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings which may be dimensioned to engage the walls of the vessels. Other less stiff helically coiled devices have been described, as well as those involving woven braids.

For instance, U.S. Pat. No. 4,994,069, to Ritchart et al., describes a vaso-occlusive coil that assumes a linear helical configuration when stretched and a folded, convoluted configuration when relaxed. The stretched condition is used in placing the coil at the desired site (by its passage through the catheter) and the coil assumes a relaxed configuration—which is better suited to occlude the vessel—once the device is so placed. Ritchart et al. describes a variety of shapes. The secondary shapes of the disclosed coils include "flower" shapes and double vortices. A random shape is described, as well. U.S. Pat. No. 5,648,082 to Sung et al., describes methods for treating arrhythmia using coils which assume random configurations upon deployment from a catheter.

Other three dimensional vaso-occlusive coils have been described. U.S. Pat. No. 5,624,461 to Mariant describes a three-dimensional in-filling vaso-occlusive coil. U.S. Pat. No. 5,639,277 to Mariant et al. describe embolic coils having twisted helical shapes and U.S. Pat. No. 5,649,949 to Wallace et al. describes variable cross-section conical vaso-occlusive coils.

U.S. Pat. No. 5,334,210 to Gianturco, describes a vascular occlusion assembly comprising a foldable material occlusion bag and a filler member, for example, a helical coil with a J-hook on the proximal end. The bag expands to form a diamond shape structure and the filler member inside the bag is forced into a convoluted configuration as it advanced into the cavity of the foldable bag.

Implantable devices using variously shaped coils are shown in U.S. Pat. No. 5,537,338 to Purdy. Purdy describes a multi-element intravascular occlusion device in which shaped coils may be employed. U.S. Pat. No. 5,536,274 to Neuss shows a spiral implant which may assume a variety of secondary shapes. Some complex shapes can be formed by interconnecting two or more of the spiral-shaped implants.

Spherical shaped occlusive devices are described in U.S. Pat. No. 5,645,558 to Horton. Horton describes how one or more strands can be wound to form a substantially hollow spherical or ovoid shape when deployed in a vessel.

There are a variety of ways of discharging shaped coils and linear coils into the human vasculature. In addition to those patents which apparently describe only the physical pushing of a coil out into the vasculature (e.g., Ritchart et al.), there are a number of other ways to release the coil at a specifically chosen time and site. U.S. Pat. No. 5,354,295 and its parent, 5,122,136, both to Guglielmi et al., describe an electrolytically detachable embolic device.

A variety of mechanically detachable devices are also known. For instance, U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vaso-occlusive coil assembly having an interlocking ball and keyway-type coupling. U.S. Pat. No. 5,304,195, to Twyford et al., shows a pusher-vaso-occlusive coil assembly having an affixed, proximately extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil.

Vaso-occlusive coils having little or no inherent secondary shape have also been described. For instance, in U.S. patent application Ser. No. 07/978,320, filed Nov. 18, 1992, entitled "Ultrasoft Embolization Coils with Fluid-Like Properties" by Berenstein et al., is found a coil having little or no shape after introduction into the vascular space.

None of these devices are stable coil designs having complex three-dimensional winding patterns. The complex winding patterns can be formed using mandrels of various designs, including a single center post having one or more side pins, a center post having one or more top pins or other random patterns having shape breaks.

SUMMARY OF THE INVENTION

This invention is a vaso-occlusive device comprising one or more vaso-occlusive members which are wound to form complex winding patterns when relaxed. The vaso-occlusive member itself may be a helically wound coil or braid typically comprising a biocompatible metal. Fibrous materials may be woven into the member or tied or wrapped onto it. The stable coils of the invention are formed by first winding a wire into a first helix; the first helix is then wound into a secondary form which is wound back onto itself, for example on a mandrel, to form two or more layers of the primary coil. The reverse winding may be on the same axis as the first winding axis or may be on a different axis. The overall form may be selected to be a variety of shapes deployed, including generally spheroid, elliptical, clover or box shapes. Generally, the shape of the relaxed configuration is formed by the outermost loops of the primary coil having the largest diameter. Loops having smaller diameters pass through the relaxed configuration. Desirably, the vaso-occlusive device is of a size and shape suitable for fitting snugly within a vascular cavity (e.g., an aneurysm, or perhaps, near a fistula). The stiffness of the various parts of the coil may be selected to enhance the utility of the device for specific applications. Fibrous materials may be woven into the member or tied or wrapped onto it.

The device is used simply by temporarily straightening the device and introducing it into a suitable catheter, the catheter already having been situated so that its distal opening is within the mouth of the vascular cavity or opening to be filled. The device is then pushed through the catheter and, upon its ejection from the distal end of the catheter into the vascular cavity, assumes its relaxed shape. The relaxed configuration of a device deployed into the body may be different than a device deployed in the open, due to constraints of vessels and the like.

The device is typically used in the human vasculature to form emboli but may be used in any site in the human body where an occlusion such as one produced by the inventive device is needed.

BRIEF DESCRIPTION OF THE DRAWINGS

FIGS. 3A and 3B are top and side views of a coil wound around a mandrel suitable for making a device according to the present invention. The mandrel is a round center post, four top-pin design.

FIGS. 4A, 4B, 4C and 4D show coils made using the mandrel of FIGS. 3A and 3B.

FIGS. 7A and 7B are side views of a coil wound around a mandrel suitable for making a device according to the present invention. The mandrel is a round center post, round staggered side-pin design. FIG. 7C shows a coil made using the mandrel of FIGS. 7A and 7B.

FIGS. 9A and 9B are side and top views of a coil wound around a mandrel suitable for making a device according to the present invention. The mandrel is a round center post, four round side-pin design.

FIGS. 10A and 10B show the relaxed configuration of coils made using the mandrels of FIGS. 9A and 9B.

DESCRIPTION OF THE INVENTION

Throughout this application, various publications, patents, and published patent applications are referred to by an identifying citation. The disclosure of the publications, patents, and published patent specifications referenced in this application are hereby incorporated by reference into the present disclosure to more fully describe the state of the art to which this invention pertains.

The complex coil designs of the present invention are particularly useful in treating aneurysms. The shapes described herein provide an improved blood flow baffle design at the neck and dome of the aneurysm, thereby providing extra protection for aneurysms which because of their fragility cannot be densely packed with other coil types. The basket-shaped coil, for instance, is easily packed into the aneurysm. The stability of the coils of the present invention reduces the incidence of coil compaction, a phenomena that may occur over time when coils move back to the shape of their first configuration. In addition, each stable coil of the present invention can fit a variety of aneurysms.

Figure 1:
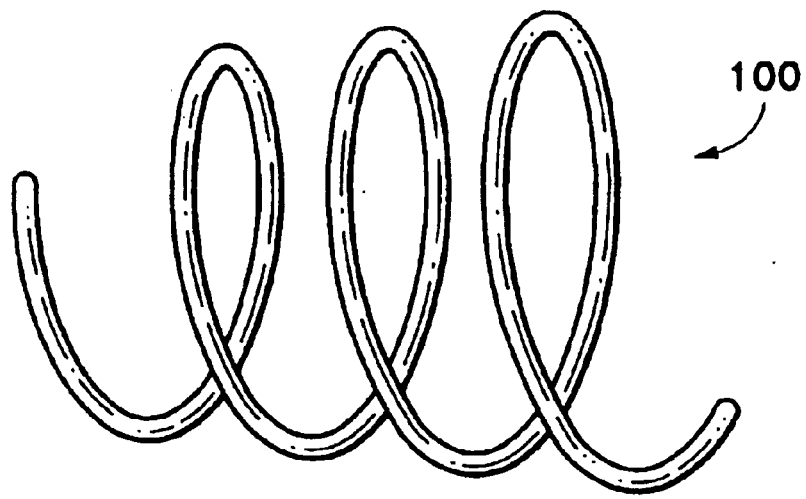
FIG. 1 shows the relaxed configuration of a conventional helical coil.

FIG. 1 shows an overview of the relaxed configuration of a helically wound coil (100) as it can appear after deployment. Note that the primary form is a helical coil. The coil (100) is 7 mm in diameter and 20 cm long.

Figure 2:
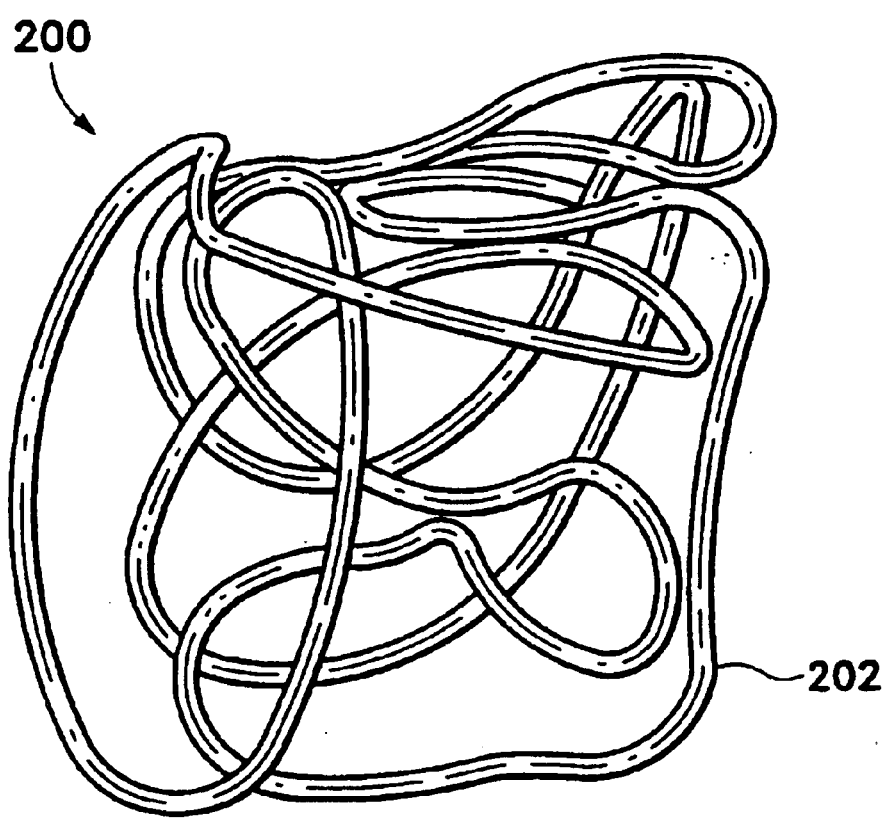
FIG. 2 shows the relaxed configuration of a coil made according to the invention using a helical coil.

FIG. 2 shows one highly desirable variation of the stable coils of this invention—a generally spherical coil (200). The variation shown would been formed on a mandrel such as those depicted herein. The coil (200) is the same diameter (7 mm) and length (20 cm) as the standard coil shown in FIG. 1, but provides a three-dimensional structure in which many loops or strands pass through the interior of the structure. The overall device (200) is made up of a primary coil which has been initially wound in a linear strand form and then wound into a secondary form which assumes the relaxed, three-dimensional configuration shown.

The material used in vaso-occlusive member (202) may be any of a wide variety of materials; preferably, the wire is a radio-opaque material such as a metal or a polymer. Suitable metals and alloys for the wire making up the primary coil include the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biologically inert. Highly preferred is a platinum/tungsten alloy.

The wire may also be of any of a wide variety of stainless steels if some sacrifice of radiopacity may be tolerated. Very desirable materials of construction, from a mechanical point of view, are materials which maintain their shape despite being subjected to high stress. Certain "super-elastic alloys" include nickel/titanium alloys (48–58 atomic % nickel and optionally containing modest amounts of iron); copper/zinc alloys (38–42 weight % zinc); copper/zinc alloys containing 1–10 weight % of beryllium, silicon, tin, aluminum, or gallium; or nickel/aluminum alloys (36–38 atomic % aluminum). Particularly preferred are the alloys described in U.S. Pat. Nos. 3,174,851; 3,351,463; and 3,753,700. Especially preferred is the titanium/nickel alloy known as "nitinol". These are very sturdy alloys which will tolerate significant flexing without deformation even when used as a very small diameter wire.

If a superelastic alloy such as nitinol is used in the device, the diameter of the coil wire may be significantly smaller than that used when the relatively more ductile platinum or platinum/tungsten alloy is used as the material of construction.

Finally, the overall diameter of the device (200) is generally between 3 and 20 millimeters. Advantageously, many different size aneurysms can be treated by one stable coil of the present invention. Of course, the device may be used with a wide range of diameters for this an other anatomical applications.

The coils may be made of radiolucent fibers or polymers (or metallic threads coated with radiolucent or radiopaque fibers) such as Dacron (polyester), polyglycolic acid, polylactic acid, fluoropolymers (polytetrafluoro-ethylene), Nylon (polyamide), or even silk. Should a polymer be used as the major component of the vaso-occlusive member, it is desirably filled with some amount of a known radiopaque material such as powdered tantalum, powdered tungsten, bismuth oxide, barium sulfate, and the like.

Generally speaking, when the device is formed of a metallic coil as the vaso-occlusive member and that coil is a platinum alloy or a superelastic alloy such as nitinol, the diameter of the wire used in the production of the coil will be in the range of 0.0005 and 0.006 inches. The wire of such diameter is typically then wound into a primary coil having a primary diameter of between 0.005 and 0.025 inches. Preferably, the primary coil is wound into a helical shape (FIG. 1). For most neurovascular indications, the preferable diameter is 0.010 to 0.018 inches. We have generally found that the wire may be of sufficient diameter to provide a hoop strength to the resulting device sufficient to hold the device in place within the chosen body cavity without distending the wall of the cavity and without moving from the cavity as a result of the repetitive fluid pulsing found in the vascular system.

The axial length of the primary shape will usually fall in the range of 0.5 to 100 cm, more usually 2 to 40 cm. Depending upon usage, the coil may well have 10–75 turns per centimeter, preferably 10–40 turns per centimeter. The device may also be made in other dimensions. However, only dimensions suitable for use in occluding sites within the human body are included in the scope of this invention.

The variation shown in the Figures is a "coil of a coil." In other words, as used herein, the "first configuration" or "primary configuration" refers to the structure obtained when a wire is shaped into a coil, for example, as a strand of a linear helically wound coil. The "secondary configuration" refers to the structures obtained when at least one strand of the first configuration is further shaped, for example, by winding around a mandrel. The relaxed configuration refers to the three-dimensional configuration assumed by the secondary configuration after it has been deployed from the catheter. The relaxed configuration may be different depending on whether the device is deployed into the open or whether it is deployed into a body cavity which may influence the three-dimensional structures. The relaxed configurations generally comprise overlapping and intertwining loops or ovals of the strand of the first configuration. The loops or ovals can form a closed structure such as an "O" shape (e.g., circle, oval, etc.) or can be open such as a "C" or "U" shape. Both open and closed loops are shown in the attached Figures.

The stable coils of the present invention have complex secondary and relaxed configurations, including spherical, ovoid, elliptical, clover and box-like shapes. The approximate diameter of the relaxed configurations can be determined from the outermost loops of the strand. In one embodiment, the complex, relaxed configurations can be substantially hollow or cage-like in configuration.

In a preferred embodiment, one or more loops (or ovals) comprising the relaxed, three-dimensional structure of the device passes through the interior of the three-dimensional structure, away from the outer edge of the diameter, providing an overall meshed or net-like appearance. Generally, the loops will have a diameter less than diameter of the overall structure (which is also the diameter of the body cavity). Preferably, greater than about 25% of the loops have a diameter less than the overall structure or cavity, more preferably greater than about 50% and even more preferably greater than about 90%. Similarly, more than 10% of the strand making the up the loops which comprise the three-dimensional relaxed configuration is in the inner 15% of the diameter of the device, as shown in the Figures herein.

Another important feature of the claimed invention is that the coils are stable when deployed. Over time, many conventional vaso-occlusive devices move back to their "coin-stacked" shape and thereby provide less occlusiveness. The coil of the present invention, however, has a complex, in vivo shape that is similar to its annealed memory, making it less likely that the coil will lose its shape over time.

The procedure for winding the coil will be known to those in the art. Although methods for production of the inventive devices may be apparent to the skilled worker based upon our description of the device, one method for winding is described herein. A portion of wire is first wound to produce a linear coil. Preferably, the wire is solid and, when wound, produced a coil having one lumen. The linear coil is then wound onto a mandrel. As disclosed in detail below, mandrels used to form the stable coils of the present invention may be of variety of shapes. In one embodiment, the mandrel comprises a center post having one or more side pins. In another embodiment, the mandrel comprises a center post having one or more top pins. In these embodiments, the center post can be round, square, elliptical, rubix (box-like), clover or otherwise shaped. Preferably, the center post is round, square, rubix or clover.

The one or more side or top pins can also be formed in a variety of shapes as shown in the Figures, for example, elliptical, round, ovoid, square or clover shaped. The pins can also be aligned along the post in rows or staggered with respect to each other. Various arrangements and shapes are shown in the Figures herein and other possibilities are known to one of ordinary skill in the art.

It is common to anneal the linear coil to prevent it from unwinding during these later fabrication steps. The linear coil is then wound around the mandrel and the complete assemblage of coil and mandrels is then subjected to an appropriate annealing step to set the secondary shape prior to disassembly of the fabrication apparatus and loading of the coil into a carrier for introduction into the delivery catheter.

The various mandrels shown are of sufficient heat resistance to allow such annealing steps. The mandrels are typically made of a refractory material such as alumina or zirconia (for heat-treating devices made of purely metallic components) or may be made of a ball of a metallic coil material. The function of the mandrels is simply to form a support for winding, not pollute the device during the heat-treatment step, and provide a specific form to the device during that heat-treatment step. A typical annealing step for a platinum/tungsten alloy would involve a 1100° F. heating step in air for about 15–20 minutes.

Should the make-up of the vaso-occlusive element not be solely metal—in that it contains readily meltable plastic or the like—the temperature at which the heat treatment takes place and would be appropriate for the material may be significantly lower and typically for a significantly shorter period of time. The flexural modulus of most plastics being significantly lower than those of metals, the bulk of the polymer-based device will be significantly larger than that of the metal-based device.

FIG. 3A is a top view of a coil (300) wound around mandrel (310). At one end of the round center post (315 in FIG. 3B) are two intersecting round posts (311, 312) that form a cross shaped structure (320). Four round pins (321, 322, 323, 324) extend from the intersection (320) of the round posts comprising cross-shaped structure at the end of the center post. FIG. 3B is a side view of the coil (300) wound around the four round pins (321, 322, 323, 324) extending from the cross-shaped structure (320) at the end of the center post (315). The mandrel shown in FIGS. 3A and 3B forms coils having a "four pintop omega" configuration.

FIGS. 4A, 4B, 4C and 4D show relaxed configurations of coils which were formed using the four pintop omega mandrels shown in FIGS. 3A and 3B. FIG. 4 shows that it is clearly not necessary that the coil's three-dimensional shape be precisely shaped as the mandrel with pin structures, but, rather, that various space-filling complex and stable secondary structures are formed.

Figure 5A:
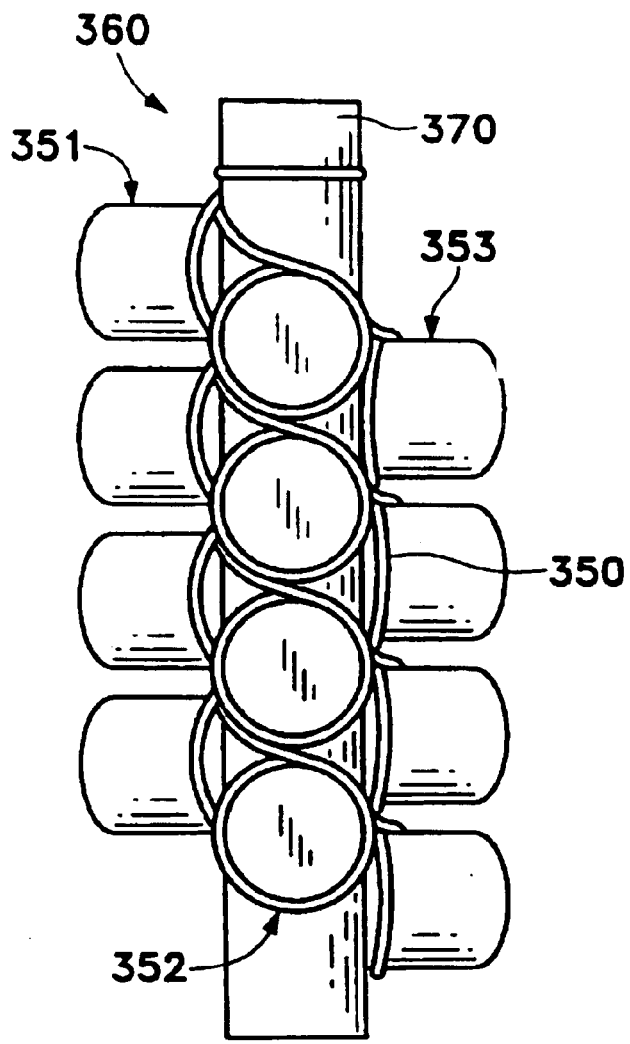
FIGS. 5A and 5B are side view of a coil wound around a mandrel suitable for making a device according to the present invention. The mandrel is a round center post, round stagger side-pin design.
Figure 5B:
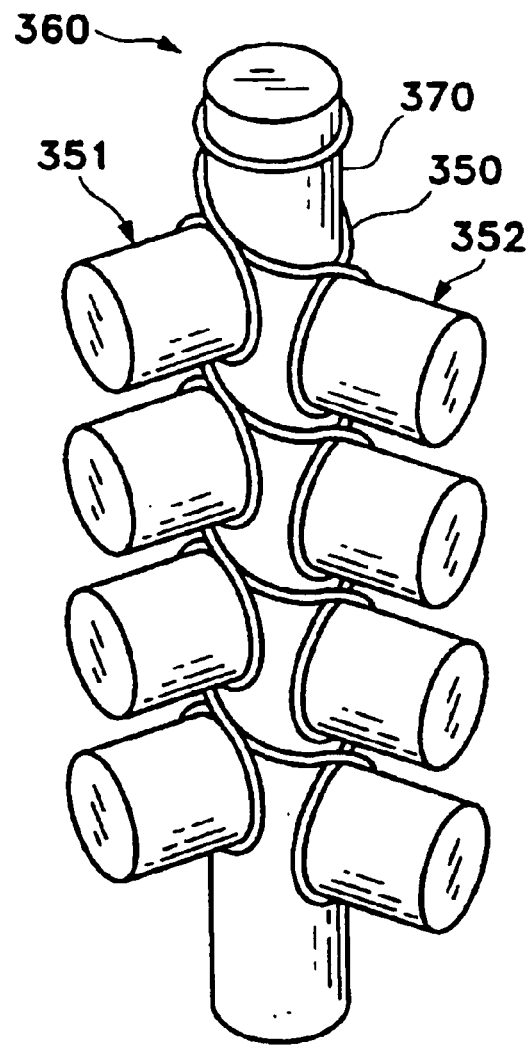

FIG. 5A is side view of a coil (350) wound around a mandrel 360) made up of a center post (370) having a three rows of round pins (351, 352, 53) staggered around the center post (370). Each row of pins is shown with our pins. FIG. 5B shows the coil and mandrel of FIG. 5A rotated approximately 45° so that the coil (350) wrapped around the round pins (351, 352, 353) is more easily seen.

Figure 6:
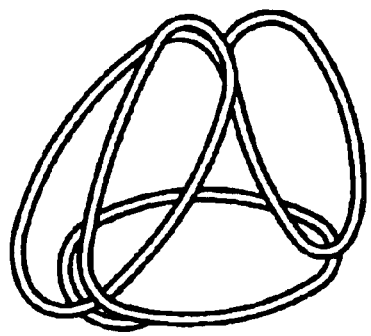
FIG. 6 shows a coil made using the mandrel of FIGS. 5A and 5B.

FIG. 6 shows the relaxed configuration of a coil formed using the three-pin round staggered mandrel shown in FIGS. 5A and 5B.

FIGS. 7A and 7B shows a mandrel (400) having three rows of pins (401, 402, third row not shown) staggered around a center post (404) and having another pin (405) offset from the staggered rows. A coil (420) is shown wrapped around the pins (401, 401, 405) and center post (404). Each row is shown with five pins. FIG. 7C shows the relaxed configuration of a coil formed on the mandrel of FIGS. 7A and 7B.

Figure 8A:
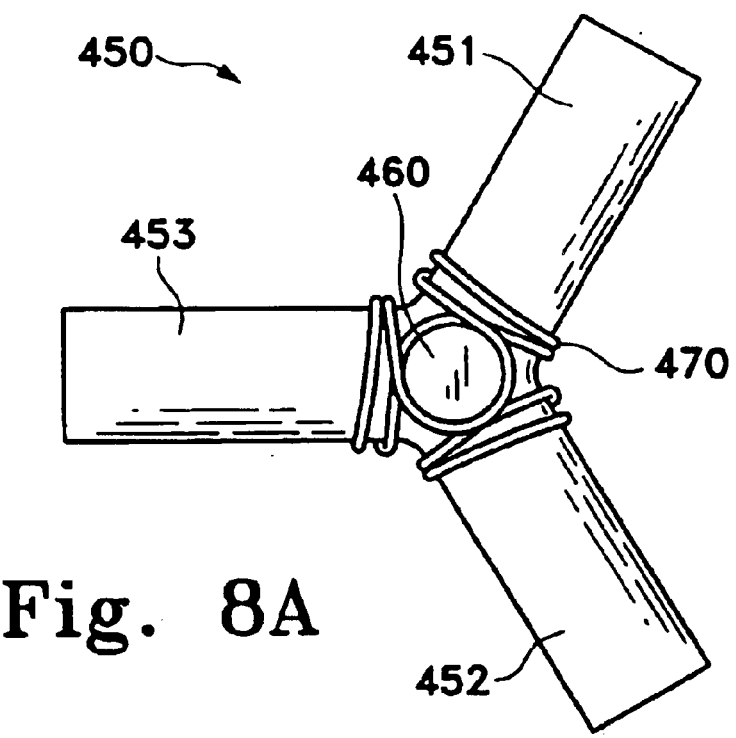
FIGS. 8A and 8B are top and side views, respectively of a coil wound around a mandrel suitable for making a device according to the present invention. The mandrel is a round center post, round side-pin design.
Figure 8B:
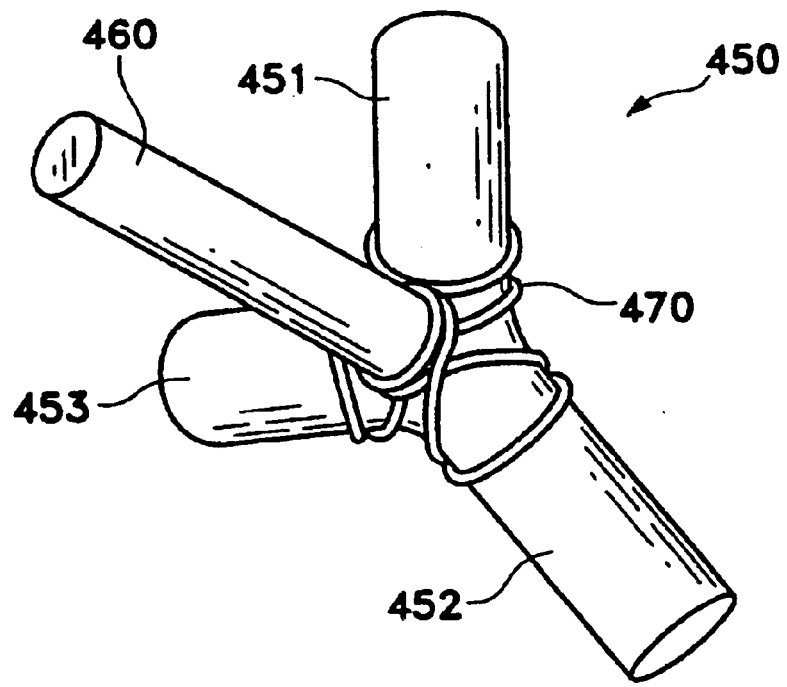

FIGS. 8A and 8B show another variation of stable coil of the present invention formed using a "three pin round cross mandrel." The mandrel (450) comprises a round center post (460) with three round side pins (451, 452, 453) positioned at approximately 120° relative to each adjacent pin. The coil (470) is shown wrapped around the pins (451, 452, 453) and center post (460).

FIGS. 9A and 9B show a coil being formed using a "four pin round box shape coil." The mandrel (500) is made up a round center post (510) with four round side-pins (511, 512, 513, 514) extending from the center post (510). The four round side-pins are positioned at approximately 90° relative to each adjacent pin. The coil (520) is shown wrapped around the mandrel.

FIG. 10A is atop view and FIG. 10B is a side view of a coil formed using the mandrel shown in FIGS. 9A and 9B.

Figure 11A:
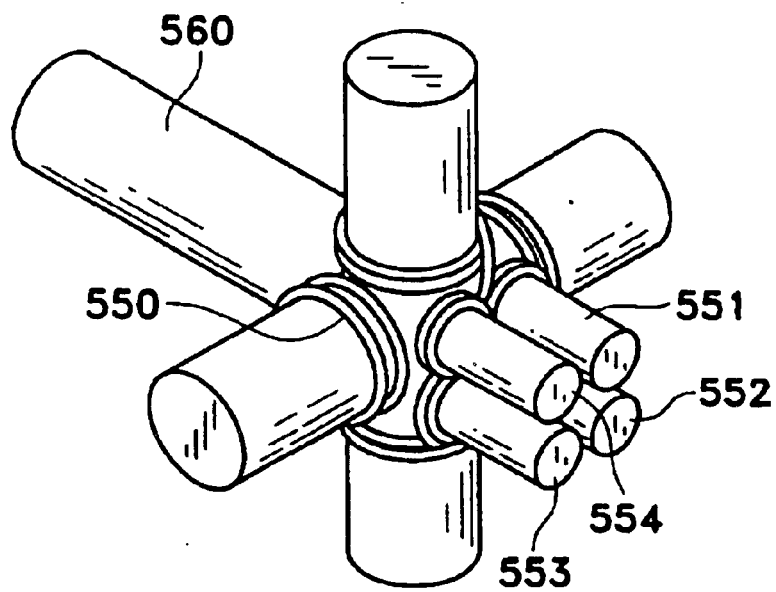
FIGS. 11A and 11B are side and top views of a coil wound around a mandrel suitable for making a device according to the present invention. The mandrel is a square center post, four round side-pin design.
Figure 11B:
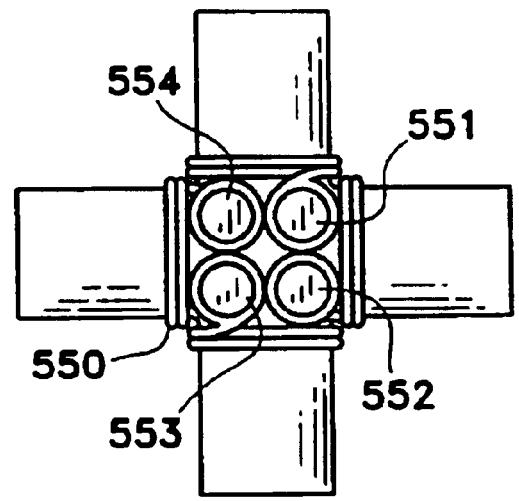

FIGS. 11A and 11B show side and top views, respectively, of a mandrel having a round center post (560) with four round top pins (551, 552, 553, 554) on the top of the post (560). The coil (550) is then wrapped around the four round tops pins.

Figure 12:
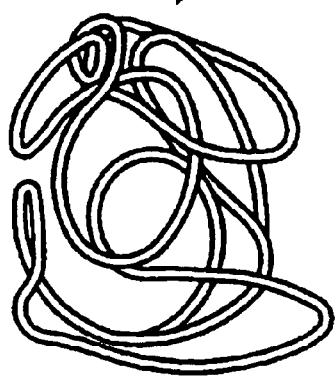
FIG. 12 shows the relaxed configuration of a coil made using the mandrels of FIGS. 11A and 11B.

FIG. 12 shows the relaxed configuration of a coil (550) formed using the mandrel shown in FIGS. 11A and 11B.

Figures 13A, 13B:
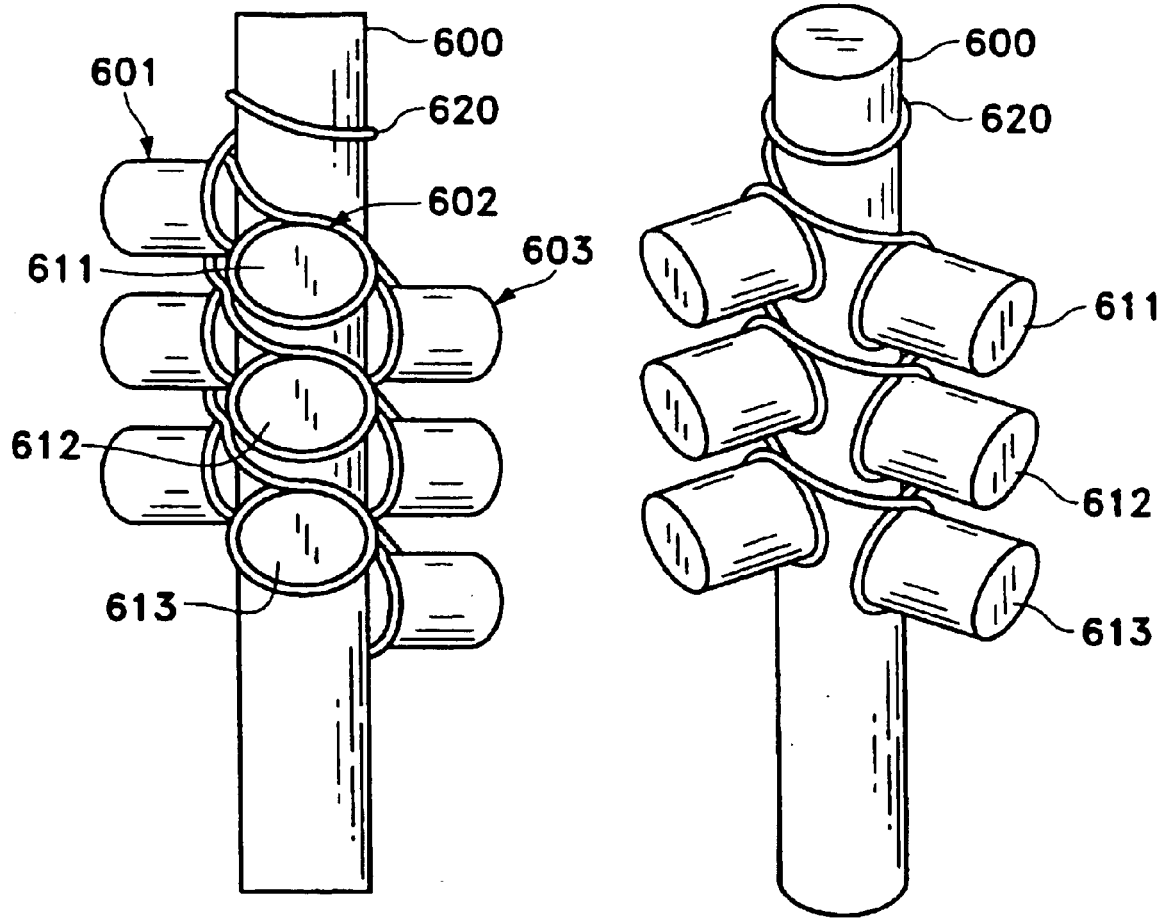
FIGS. 13A and 13B are side views of a coil wound around a mandrel suitable for making a device according to the present invention. The mandrel is a round center post, elliptical, staggered side-pin design.

FIGS. 13A and 13B show side views of a mandrel having a round center post (600) with rows of elliptical side pins (601, 602, 603). Each row of elliptical side pins is staggered with respect to the others. Each row is shown with three elliptical side pins (611, 612, 613). The coil (620) is shown wrapped around the elliptical side pins.

Figure 14:
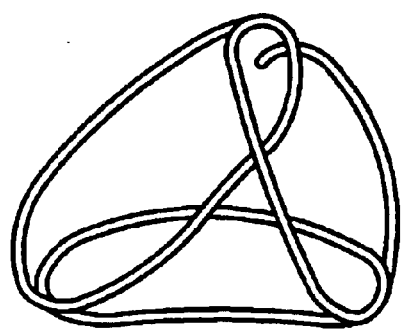
FIG. 14 shows the relaxed configuration of a coil made using the mandrels of FIGS. 13A and 13B.

FIG. 14 shows a top view of a relaxed configuration of a coil (620) formed using the mandrel shown in FIGS. 13A and 13B.

Figure 15B:
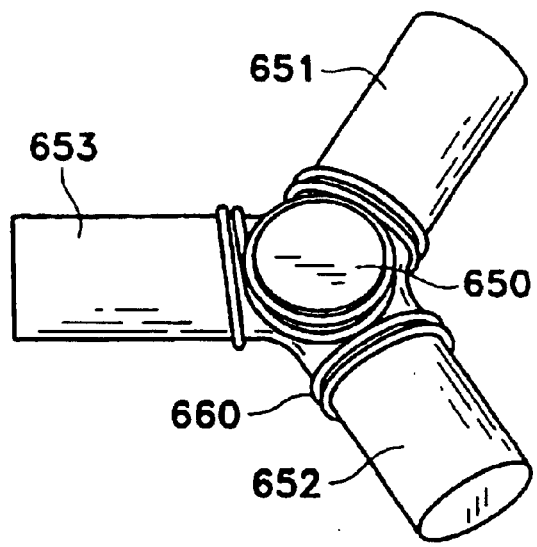
FIGS. 15A and 15B are side and top views of a coil wound around a mandrel suitable for making a device according to the present invention. The mandrel is a round center post, three elliptical side-pin design.
Figure 15A:
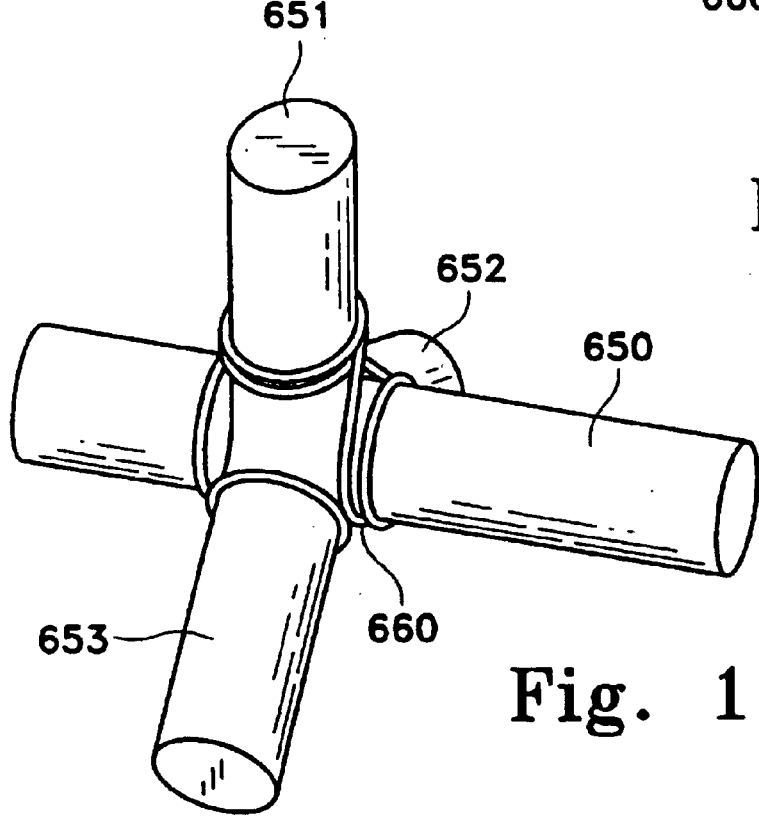

FIGS. 15A and 15B are side and top views, respectively, of a mandrel having a round center post (650) with three elliptical side pins (651, 652, 653) positioned at approximately 120° relative to the each other pin. The coil (660) is wrapped around the pins (651, 652, 653) and center post (650).

Figure 16:
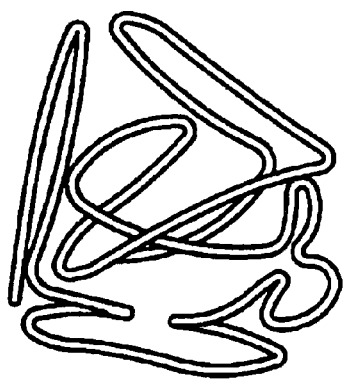
FIG. 16 shows the relaxed configuration of a coil made using the mandrels of FIGS. 15A and 15B.

FIG. 16 shows one part of a coil (660) formed using the mandrel shown in FIGS. 15A and 15B.

Figure 17A:
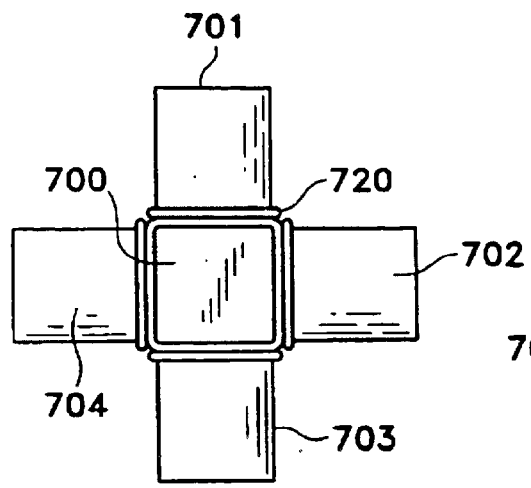
FIGS. 17A and 17B are top and side views of a coil wound around a mandrel suitable for making a device according to the present invention. The mandrel is a square center post, four round side-pin design.
Figure 17B:
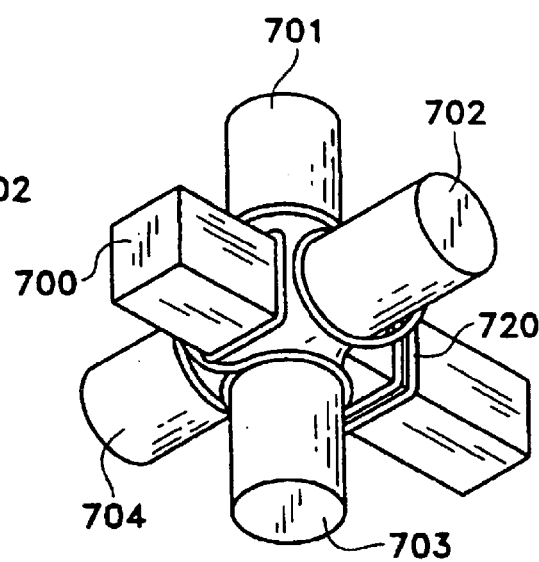

FIGS. 17A and 17B are top and side views, respectively, of a mandrel having a square center post (700) with four round side pins (701, 702, 703, 704) positioned at approximately 90° relative to two adjacent pins. The coil (720) is wrapped around the round side pins (701, 702, 703, 704) and the square center post (700).

Figure 18A:
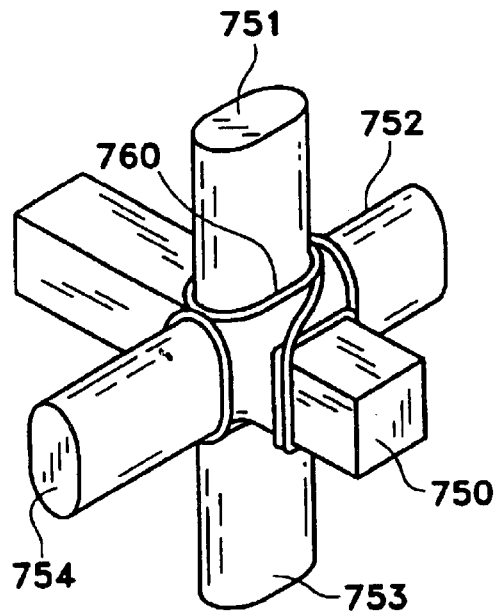
FIGS. 18A and 18B are side and top views of a coil wound around a mandrel suitable for making a device according to the present invention. The mandrel is a square center post, four elliptical side-pin design.
Figure 18B:
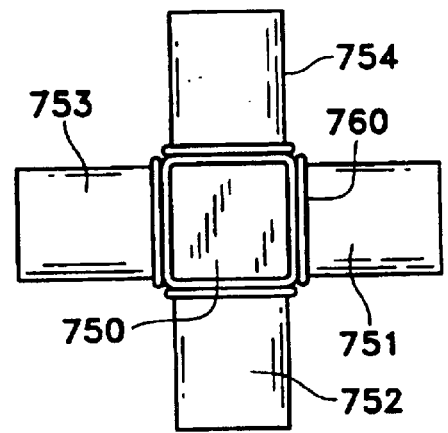

FIGS. 18A and 18B are side and top views, respectively, of a mandrel having a square center post (750) with four elliptical side pins (751, 752, 753, 754) positioned at approximately 90° relative to two adjacent pins. The coil (760) is wrapped around the elliptical side pins (751, 752, 753, 754) and the square center post (750).

Figure 19A:
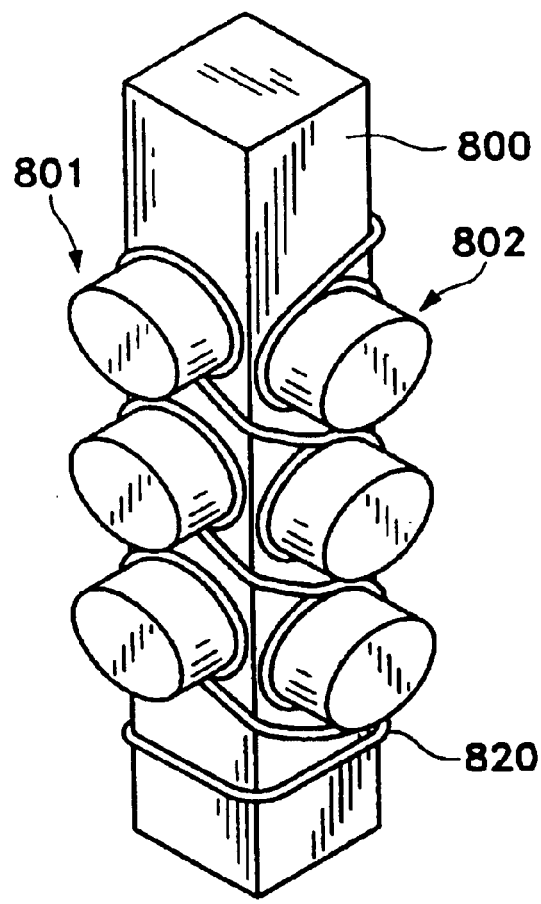
FIGS. 19A and 19B are side views of a coil wound around a mandrel suitable for making a device according to the present invention. The mandrel is a square center post, four staggered elliptical side-pin design.
Figure 19B:
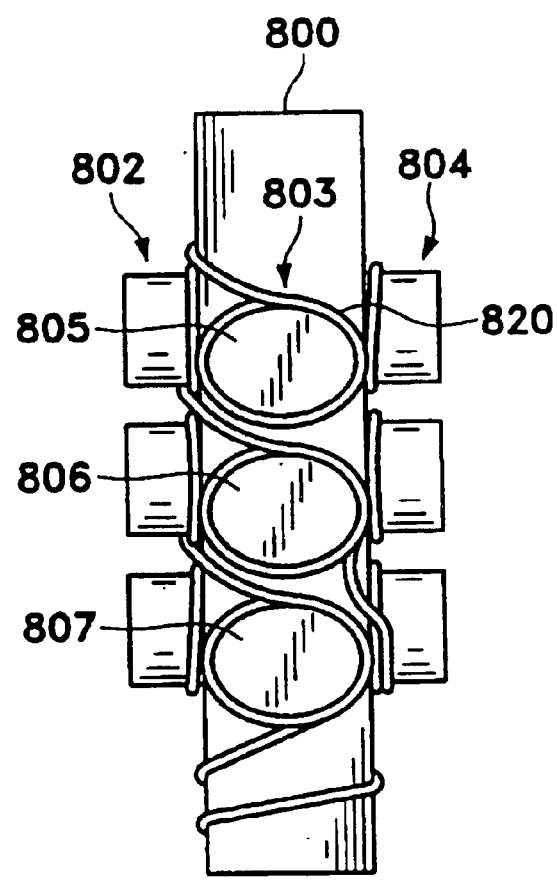
Figure 20A:
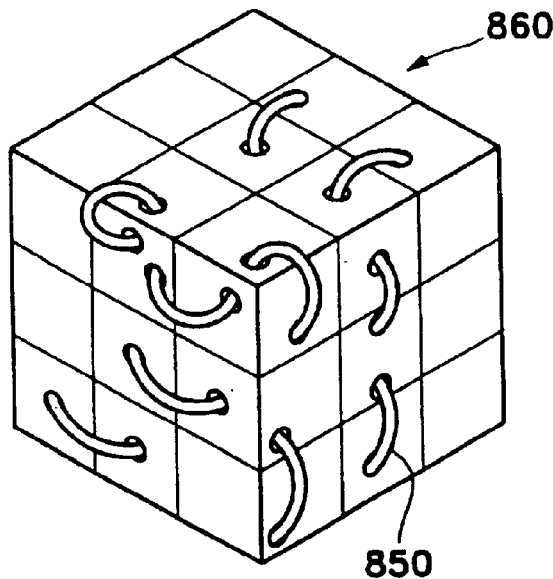
FIGS. 20A, 20B, 20C and 20D are side (20A, 20B) and top (20C, 20D) views of a randomly would coil on a mandrel suitable for making a device according to the present invention. The mandrel is a box-like (rubix) shape.
Figure 20B:
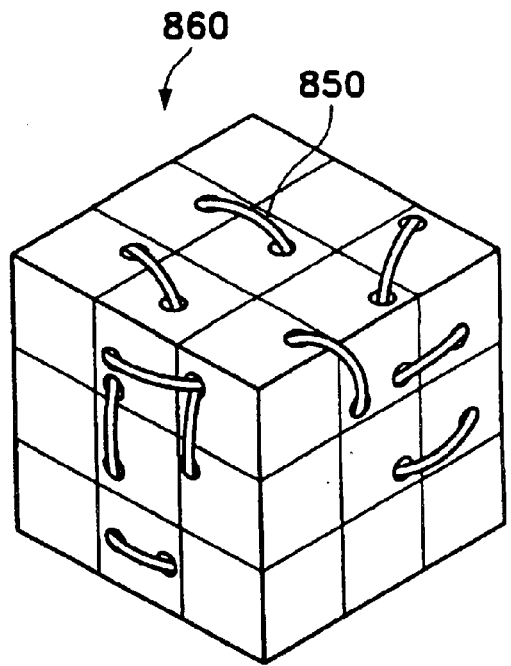
Figure 20C:
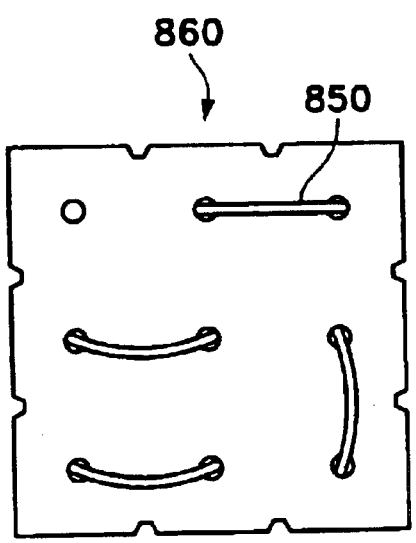
Figure 20D:
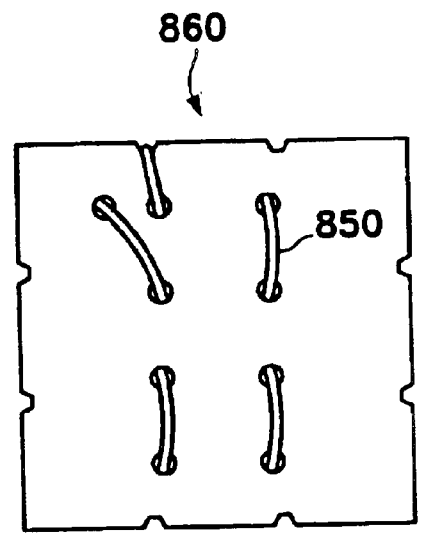

FIGS. 19A and 19B are two side views of a mandrel having a square center post (800) with four staggered rows of elliptical side pins (801, 802, 803, 804) positioned on each side of the square. Each row is shown with three pins (805, 806, 807). The coil (820) is wrapped around the pins and the square post (800).

FIGS. 20A, 20B, 20C and 20D shown various random winding patterns of a coil (850) around a rubix shaped mandrel (860).

Figure 21A:
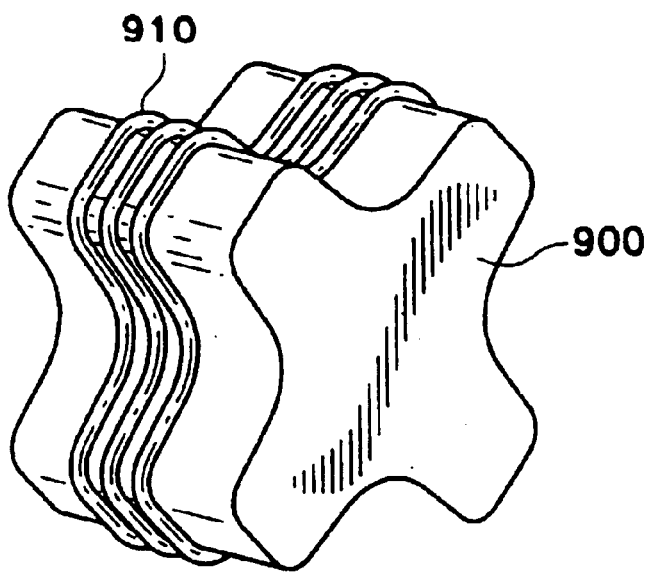
FIGS. 21A and 21B are side and top views of a coil wound around a mandrel suitable for making a device according to the present invention. The mandrel is a clover shape.
Figure 21B:
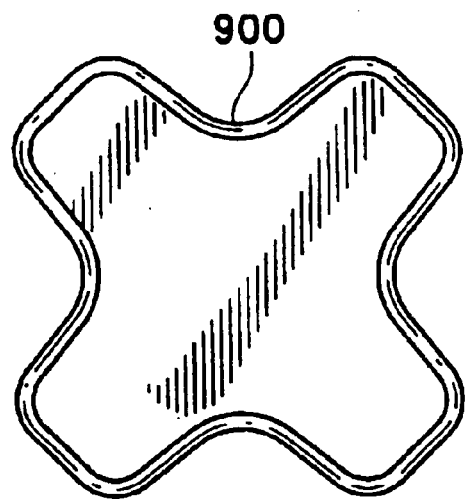

FIGS. 21A and 21B show side and top views of a clover shaped mandrel, essentially a clover shape center post (900). The coil (910) is wrapped around the center post (900).

Figure 22A:
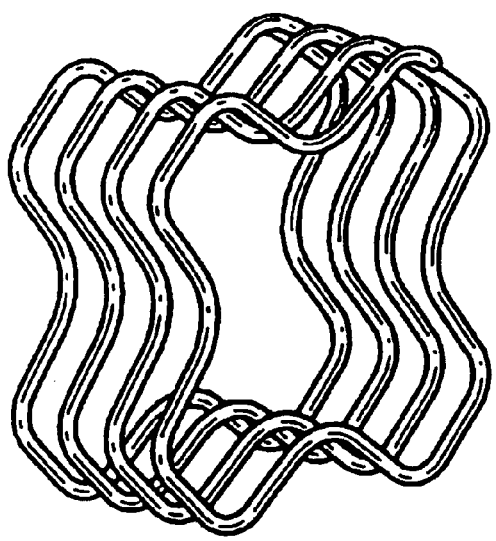
FIGS. 22A and 22B show the relaxed configuration of coils made using the mandrels of FIGS. 21A and 21B.
Figure 22B:
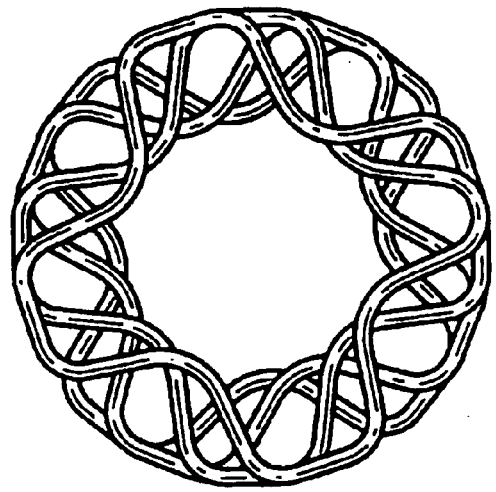

FIGS. 22A and 22B show the relaxed configurations of coils formed using the mandrel shown in FIGS. 21A and 21B.

Figure 23A:
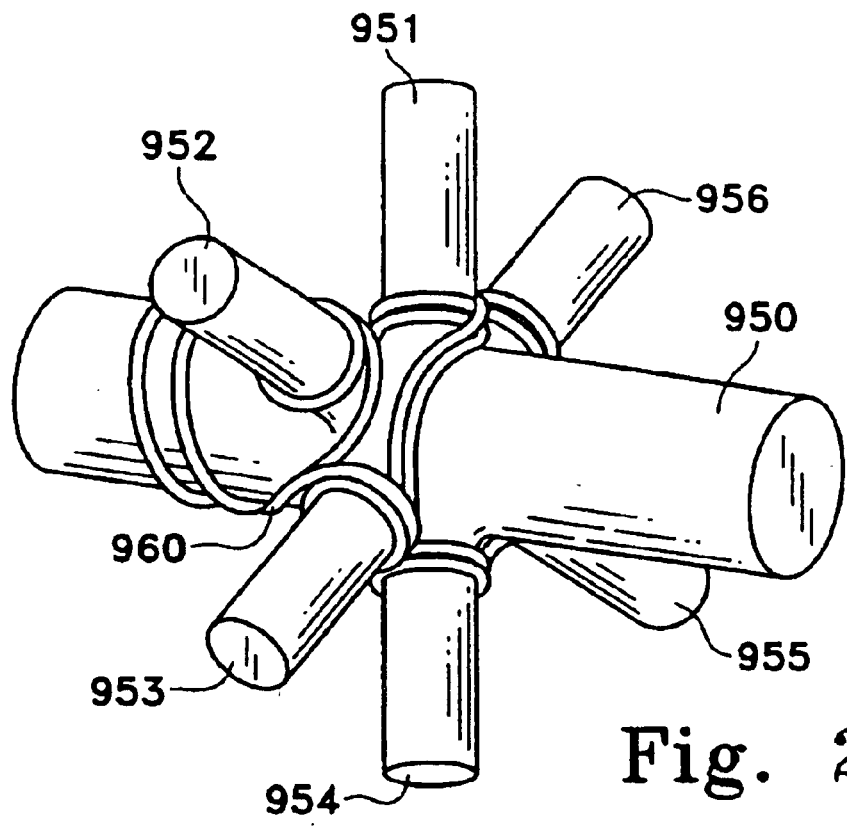
FIGS. 23A and 23B show side and top views, respectively, of a mandrel having a round center post and six round side pin design.
Figure 23B:
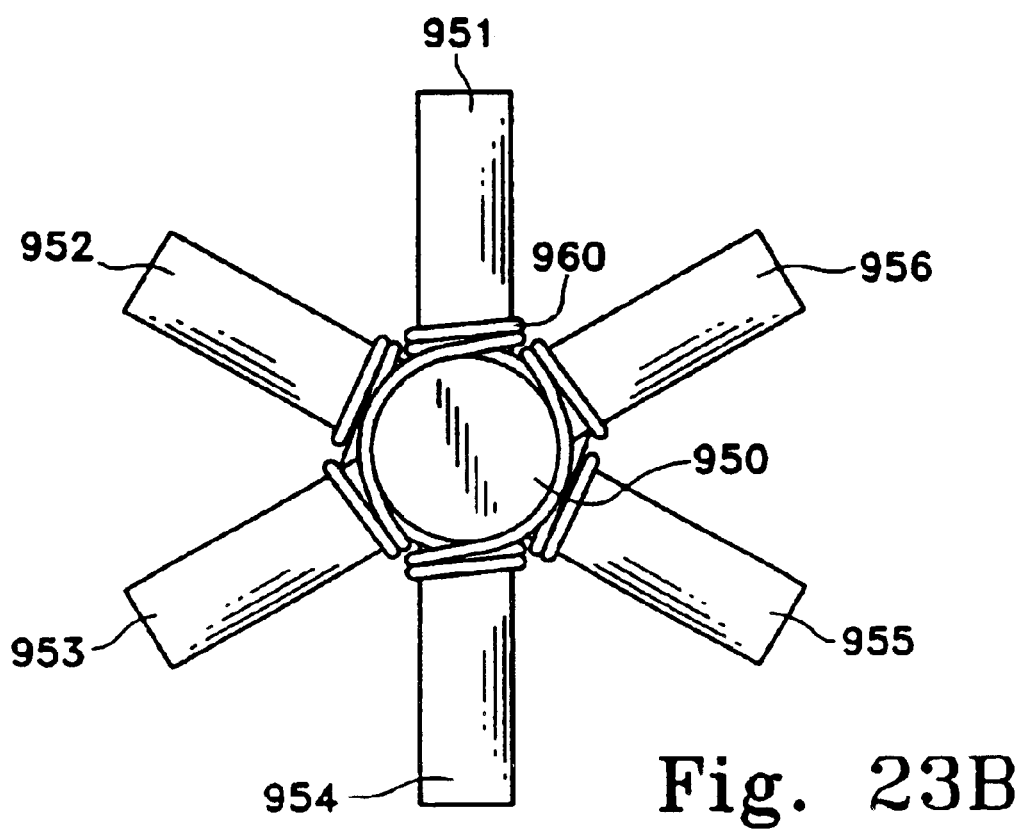

FIGS. 23A and 23B show side and top view, respectively, of a mandrel having a round center post (950) with six round side pins (951, 952, 953, 954, 955, 956). The six pins are spaced approximately 30° from each adjacent pin. The coil (960) is shown wound around the center post (950) and side pins.

Also contemplated in this invention is the attachment of various fibrous materials to the inventive coils for the purpose of adding thrombogenicity to the resulting assembly. The fibrous materials may be attached in a variety of ways. A series of looping fibers may be looped through or tied to coil and continue axially down the coil. Another variation is by tying the tuft to the coil. Tufts may be tied at multiple sites through the coil to provide a vast area of embolus forming sites. The primary coil may be covered by a fibrous braid. The method for producing the former variation is described in U.S. Pat. Nos. 5,226,911 and 5,304,194 to Chee. The method of producing the fibrous braid is described in U.S. Pat. No. 5,382,259, issued Jan. 17, 1995, to Phelps and Van.

The complex stable coils of the invention are deployed by methods known in the art. One common deployment method for introduction of the inventive vaso-occlusive devices described here. It may be observed that these procedures are not significantly different than those described in the Ritchart et al. patent mentioned above. The major difference in the procedure is the ability of the vaso-occlusive device to form the secondary shapes discussed above as the coil exits the catheter. Specifically, a delivery catheter is placed within the opening of an aneurysm found in an artery. The vaso-occlusive device is within the catheter and can be forced to exit the catheter. As the coil exits the distal end of the catheter (210) it "self-winds" to begin forming the complex structure. The catheter is withdrawn, leaving the vaso-occlusive device within the aneurysm.

Because of the configurations of these devices, the procedure of introducing them into an open space in the human body involves placement of the delivery catheter tip at that space and the introduction of a coil that self-winds into a series of loops or ovals, each having a larger diameter which is significantly smaller than the open space to be filled. The filling of the space, therefore, place by passage of the coil through a central region of the space (e.g., aneurysm), rather than along its wall.

Modification of the above-described variations of carrying out the invention that would be apparent to those of skill in the fields of medical device design generally, and vaso-occlusive devices specifically, are intended to be within the scope of the following claims.

We claim as our invention:

1. A vaso-occlusive device comprising a strand of a member that forms a series of loops, each loop lying approximately within a plane that forms an angle with a plane of an adjacent loop in the series, wherein one of the loops in the series is formed by winding the strand of member in a first direction, with an adjacent loop in the series formed by winding the strand of member in a second direction to thereby provide an inflection point between the respective one of the series of loops and the adjacent loop in the series.

2. The vaso-occlusive device of claim 1, wherein the member comprises at least one of a helically wound coil and a braided tubular member.

3. The vaso-occlusive device of claim 1, wherein the member comprises one or a combination or sub-combination of platinum, palladium, rhodium, gold, tungsten, and their alloys.

4. The vaso-occlusive device of claim 1, wherein the member comprises an alloy selected from a group consisting of stainless steels and super-elastic alloys.

5. The vaso-occlusive device of claim 4, wherein the member comprises nitinol.

6. The vaso-occlusive device of claim 1, wherein the member comprises a deployment tip attached to an end of the member.

7. The vaso-occlusive device of claim 6, wherein the deployment tip comprises an electrolytically detachable end adapted to detach from a restraining member.

8. The vaso-occlusive device of claim 1, wherein each loop travels at least one revolution.

9. The vaso-occlusive device of claim 1, wherein the series of loops forms a three-dimensional configuration.

10. The vaso-occlusive device of claim 9, wherein the three-dimensional configuration is shaped to occupy a body cavity having a diameter.

11. The vaso-occlusive device of claim 10, each loop having a diameter less than 90% of the diameter of the body cavity.

12. The vaso-occlusive device of claim 10, each loop having a diameter less than 50% of the diameter of the body cavity.

13. The vaso-occlusive device of claim 10, each loop having a diameter less than 25% of the diameter of the body cavity.

14. The vaso-occlusive device of claim 9, wherein the three-dimensional configuration is spherical, oval, elliptical, clover, box-like, or a combination or sub-combination thereof.

15. The vaso-occlusive device of claim 1, wherein the strand of the member comprises a coil.

16. A vaso-occlusive device comprising at least one substantially linear stand of a vaso-occlusive member wound into a three-dimensional relaxed configuration, the three dimensional relaxed configuration comprising a first loop, a second loop, a third loop, and a fourth loop, wherein the second loop is approximately perpendicular to the first loop, the third loop is approximately perpendicular to the first and the second loops, and the fourth loop is approximately perpendicular to the second and the third loops.

17. The vaso-occlusive device of claim 16, the three dimensional relaxed configuration further comprising a fifth loop that is approximately perpendicular to the first, third, and fourth loops.

18. The vaso-occlusive device of claim 17, the three dimensional relaxed configuration further comprising a sixth loop that is approximately perpendicular to the first, second, fourth, and fifth loops.

19. The vaso-occlusive device of claim 18, the three dimensional relaxed configuration further comprising additional loops, wherein each of the additional loops is approximately perpendicular to an adjacent loop.

20. The vaso-occlusive device of claim 16, wherein the relaxed configuration is self-forming when released from a restraining member.

21. The vaso-occlusive device of claim 16, wherein the vaso-occlusive member comprises one of a helically wound, coil and a braided tubular member.

22. The vaso-occlusive device of claim 16, wherein each of the loops travels at least one revolution.

23. The vaso-occlusive device of claim 16, wherein the loops alternate between clockwise and counterclockwise orientations.

24. The vaso-occlusive device of claim 16, wherein the strand of the vaso-occlusive member comprises a coil.

25. A vaso-occlusive device comprising a strand of a member that forms a first loop, a second loop that is directly connected to the first loop such that no loop is formed between the first and the second loops, and a third loop that is directly connected to the second loop such that no loop is formed between the second and the third loops;
wherein the first loop lies approximately within a first plane, the second loop lies approximately within a second plane, and the third loop lies approximately within a third plane, the first plane forming a non-zero degree angle with the second plane, and the second plane forming a non-zero degree angle with the third plane, and wherein the first, second, and third planes are oriented such that they collectively form a substantially three-dimensional, non-planar configuration.

26. The vaso-occlusive device of claim 25, wherein the first, second, and third loops form a three-dimensional configuration.

27. The vaso-occlusive device of claim 26, wherein the three-dimensional configuration is spherical, oval, elliptical, clover, box-like, or a combination or sub-combination thereof.

28. The vaso-occlusive device of claim 25, wherein the member comprises one or a combination or sub-combination of platinum, palladium, rhodium, gold, tungsten, and their alloys.

29. The vaso-occlusive device of claim 25, wherein the member comprises a deployment tip attached to an end of the member.

30. The vaso-occlusive device of claim 29, wherein the deployment tip comprises an electrolytically detachable end adapted to detach from a restraining member.

31. The vaso-occlusive device of claim 25, wherein each loop travels at least one revolution.

32. The vaso-occlusive device of claim 25, wherein the strand of the member comprises a coil.

33. A vaso-occlusive device comprising a strand of a member that forms a first loop, a second loop that is directly connected to the first loop, and a third loop that is directly connected to the second loop,
wherein the first loop lies approximately within a first plane, the second loop lies approximately within a second plane, and the third loop lies approximately within a third plane, the first plane forming an angle with the second plane, and the second plane forming an angle with the third plane, and wherein the first loop is formed by winding the strand of member in a first direction, and the second loop is formed by winding the strand of member in a second direction to thereby provide an inflection point between the first loop and the second loop.

* * * * *